(12) United States Patent
Cazaux et al.

(10) Patent No.: US 7,670,809 B2
(45) Date of Patent: Mar. 2, 2010

(54) USE OF MUTAGENIC DNA POLYMERASE FOR PRODUCING RANDOM MUTATIONS

(75) Inventors: Christophe Cazaux, Plaisance du Touch (FR); Jean Sébastien Hoffmann, Toulouse (FR); Thierry Louat, Saint Chamond (FR); Laurence Servant, Toulouse (FR); Khalil Bouayadi, Toulouse (FR); Hakim Kharrat, Pechbusque (FR)

(73) Assignee: Millegen, Labege (FR)

( * ) Notice: Subject to any disclaimer, the term of this patent is extended or adjusted under 35 U.S.C. 154(b) by 845 days.

(21) Appl. No.: 10/416,424

(22) PCT Filed: Nov. 7, 2001

(86) PCT No.: PCT/FR01/03450

§ 371 (c)(1),
(2), (4) Date: Oct. 22, 2003

(87) PCT Pub. No.: WO02/38756

PCT Pub. Date: May 16, 2002

(65) Prior Publication Data

US 2004/0110294 A1    Jun. 10, 2004

(30) Foreign Application Priority Data

Nov. 8, 2000    (FR)    .................. 00 14333

(51) Int. Cl.
*C12P 19/34*    (2006.01)
*C12Q 1/68*    (2006.01)

(52) U.S. Cl. .......................................... 435/91.2; 435/6

(58) Field of Classification Search ...................... 435/6
See application file for complete search history.

(56) References Cited

U.S. PATENT DOCUMENTS 6,165,718 A * 12/2000 Borchert et al. ................ 435/6
6,255,062 B1 * 7/2001 Campbell et al. ............. 435/15
6,475,996 B1 * 11/2002 Cazaux et al. ................ 514/44

FOREIGN PATENT DOCUMENTS

WO    98/23733    6/1998

OTHER PUBLICATIONS

Intermolecular transferases, www.biochem.ucl.ac.uk/bsm/enzymes/ec5/ec04/index.html, pp. 1-5.*
Glick et al., The EMBO Journal, vol. 20, No. 24, pp. 7303-7312, 2001.*
Sugaya et al: Genes to Cells, vol. 7, pp. 385-399, 2002.*
Perderiset et al. Biochem. Journal, vol. 335, pp. 581-588, 1998.*
Skandalis, et al, vol. 7 (suppl), pp. 1000, Abstract 291, 1995.*
Radman, M. Nature, vol. 401, p. 866-869, Oct. 1999.*
Cadwell et al. (1992) "Randomization of genes by PCR mutagenesis" Cold Spring Harbor Laboratory 2: 28-33.
Bouayadi et al. (1997) "Overexpression of DNA polymerase β sensitives mammalian cells to 2', 3'-deoxycytidine and 3'-azido-3'-deoxythymidine" Cancer Research 57: 110-116.
Zaccolo et al. (1996) "An approach to random mutagenesis of DNA using mixture of triphosphate derivatives of nucleoside analogues" J. Mol. Biol. 255: 589-603.
Moore et al. (1996) "Direct evolution of a para-nitrobenzyl esterase for aqueous-organic solvent" Nat. Biotech. 14: 458-467.
Sweasy et al. (1993) "Detection and characterization of mammalian DNA polymerase β mutants by functional complementation in *Escherichia coli*" Proc. Natl. Acad. Sci. USA 90: 4626-4630.
Diaz et al. (1991) "PCR-mediated chemical mutagenesis of cloned duplex DNAs". Biotechniques 11: 204-211.
Horwitz et al. (1986) "Promoters selected from random DNA sequences" Proc. Natl. Acad. Sci. USA 83: 7405-7409.
Dube et al. (1989) "Mutants generated by the insertion of random oligonucleotides into the active site of the β-lactamase gene" Biochemistry 28: 5703-5707.
Stemmer W. P.C. (1994) "DNA shuffling by random fragmentation and reassembly: in vitro recombination for molecular evolution" Proc. Natl. Acad. Sci. 91: 10747-10751.
Kunkel T.A. (1985) "The mutational specificity of DNA polymerase-β during in vitro DNA synthesis" J. Biol. Chem. 260: 5787-5796.
Kunkel, T.A. (1986) "Frameshift mutagenesis by eucaryotic DNA polymerases in vitro." J. Biol. Chem. 261: 13581-13587.

(Continued)

*Primary Examiner*—Gary Benzion
*Assistant Examiner*—Cynthia B Wilder
(74) *Attorney, Agent, or Firm*—Young & Thompson

(57) ABSTRACT

The invention concerns a method for random mutagenesis comprising the replication of a DNA sequence in the presence of an efficient amount of at least a mutase, for example a Pol β, the random mutagenesis rate being at least of the order of 1 mutation for 400 base pairs. The replication product, optionally recombined and amplified, is cloned in an expression vector so as to generate mutated polypeptides which will be selected on the basis of the desired property or properties.

21 Claims, 6 Drawing Sheets

OTHER PUBLICATIONS

Beckman et al. (1985) "On the fidelity of DNA replication: manganese mutagenesis in vitro." Biochemistry 24: 5810-5817.

Robert et al. (1993) "Chromosome and gene analysis" Methods in Molecular Genetics. Adolph, K.W. Ed. 2: 295-313.

John D. Roberts et al., "Fidelity of DNA Replication in Human Cells," *Methods in Molecular Genetics*, 1993, vol. 2, pp. 295-313.

Yanbin Zhang, et al., "Human DNA polymerase K synthesizes DNA with extraordinarily low fidelity," Nucleic Acids Research, 2000, 4147-4156, vol. 28, No. 21, Oxford University Press, Lexington, KY.

Wendy P. Osheroff et al., "Minor Groove Interactions at the DNA Polymerase β Active Site Modulate Single-base Deletion Error Rates*," 2000, 28033-28038, vol. 275, No. 36, JBC Papers in Press, North Carolina.

Hubscher U et al., "Eukaryotic DNA polymerases," Abstract, 2002, 63, vol. 71, No. 133, Zurich, Switzerland.

Adonis Skandalis et al., "Enzymatic Properties of rat DNA polymerase β mutants obtained by randomized mutagenesis," Nucleic Acids Research, 2001, 2418-2426, vol. 29, No. 11, Oxford University Press, Seattle, WA.

* cited by examiner

```
                                      A
                                      A
                                      A
              A       A    A
        T  A    A G    -A    -T - - A    +A
5' T GAA TAC TGT A TG ATA ATC GTG AGG ATC CCG CAT ATA A GC TTT TCG ATC GCC TGC AGT AA C TCC ACC ATA ATG AGG AAT TCA ATC C 3'
```

Figure 3 (SEQ ID NO: 6)

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gattgaattc ctcattatgg                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgaatactgt atgataatcg                                                    20

<210> SEQ ID NO 3
<211> LENGTH: 85
<212> TYPE: DNA
<213> ORGANISM: Artificial Sequence
<220> FEATURE:
<223> OTHER INFORMATION: Primer

<400> SEQUENCE: 3
tgaatactgt atgataatcg tgaggatccc gcatataagc ttttcgatcg cctgcagtaa         60
ctccaccata atgaggaatt caatc                                              85

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
cgcgactcat gcgacgcatt acgaattcga gctcggtac                               39

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
cactcgacgc tgatgcagtg caccatatgc ggtgtg                                  36

<210> SEQ ID NO 6
<211> LENGTH: 86
<212> TYPE: DNA
<213> ORGANISM: Artificial Sequence
<220> FEATURE:
<223> OTHER INFORMATION: Primer

<400> SEQUENCE: 6
tgaatactgt atgataatcg tgaggatccc gcatataagc ttttcgatcg cctgcagtaa         60
ctccaccata atgaggaatt caatcc                                             86

USE OF MUTAGENIC DNA POLYMERASE FOR PRODUCING RANDOM MUTATIONS

FIELD OF THE INVENTION

The present invention relates to the use of one or more mutagenic DNA polymerases for modifying DNA sequences which are at least partially coding. Such a process should make it possible to rapidly obtain a large number of random mutants, and therefore mutated polypeptide (for example protein) libraries, and makes it possible to select polypeptides (for example proteins) of interest according to a predetermined phenotype. This tool is therefore directed in particular toward any experimenter wishing to modify a protein either in the context of a fundamental study or with a view to a phenotypic improvement for industrial purposes.

BACKGROUND OF THE INVENTION

Various techniques have been developed for promoting in vitro mutagenesis on DNA sequences. Among these, mention may be made of site-directed mutagenesis and random mutagenesis.

Site-directed mutagenesis is a method which consists in altering the structure of a protein, in vitro, by simple modification of targeted codons in the sequence of the DNA. Thus, amino acids can be substituted at known or supposed active sites of the protein.

Random mutagenesis in vitro consists in introducing, during a replication or recombination step, mutations distributed randomly over the sequence of a gene or of a gene fragment. The mutations can be introduced throughout the length of the coding region of a gene, or can be confined to quite specific DNA segments. Unlike site-directed mutagenesis, a precise knowledge of the structure of the protein is not necessary to carry out random mutagenesis.

Several methods of random mutagenesis have been developed.

In a first, widely implemented approach, the polymerase chain reaction (PCR) is used under conditions which promote the introduction of mutations (error-prone PCR). With Taq polymerase, the frequency of base substitution can reach $10^{-3}$, i.e. 1 substitution per 1 000 base pairs (Moore et al. (1996) "Direct evolution of para-nitrobenzyl esterase for aqueous-organic solvant" *Nat. Biotech.* 14: 458-467). In other cases, a frequency of approximately 1 substitution per 500 bases has been reached (Sweasy et al. (1993) "Detection and characterization of mammalian DNA polymerase β mutants by functional complementation in *Escherichia coli*" *Proc. Natl. Acad. Sci. USA* 90: 4626-4630; Diaz et al. (1991) "PCR-mediated chemical mutagenesis of cloned duplex DNAs". *Biotechniques* 11: 204-211).

However, this technique has several drawbacks. In particular, it requires a step in which the substrate to be modified is treated with genotoxic chemical compounds. In addition, it produces too low a rate of mutagenesis. It is not therefore suitable for the construction of a library of mutants and the rapid selection of advantageous mutants.

In another approach, use is made of oligonucleotides (for example 19 or 47 base pairs) of random sequence synthesized by a chemical process (degenerate oligonucleotides), which are inserted into a gene, preferably into the region encoding the active part of the enzyme, and used to provide a diversity of proteins. (Horowitz et al. (1986) "Promoters selected from random DNA sequences" *Proc. Natl. Acad. Sci. USA* 83: 7405-7409; Dube et al. (1989) "Mutants generated by the insertion of random oligonucleotides into the active site of the β-lactamase gene" *Biochemistry* 267: 5703-5707). This procedure requires the synthesis, also expensive, of many mutated oligonucleotides.

Yet another approach, based on the use of homologous recombination, similar to the natural process of genetic mixing which takes place during evolution, can be used. This method is called shuffling (Stemmer (1994) "DNA shuffling by random fragmentation and reassembly: in vitro recombination for molecular evolution" *Proc. Natl. Acad. Sci. USA* 91: 10747-10751). It consists in carrying out a PCR on fragments of a gene or fragments of several homologous genes, subsequent to a random digestion with DNAse I. The small fragments derived from this digestion serve as primers with respect to one another during the PCR, and lead to the introduction of random mutations by recombination. This method is laborious and takes place in several steps (digestion of the DNA, recombination by PCR in the presence of "mega-primers", etc.), which involves difficulties in implementation. It has been used in improving the activities of several enzymes such as Green Fluorescent Protein, β-lactamase, and also the arsenate detoxication operon.

The fidelity of several DNA polymerases has been tested in order to measure their mutagenic capacity. Among these, the Klenow fragment of *Escherichia coli* DNA polymerase I, T4 DNA polymerase, the T7 phage DNA polymerase sequenase, and the Taq DNA polymerase. Among all these polymerases, the Taq polymerase exhibits the least fidelity. However, the frequency of mutagenesis remains too low to envisage its use for random mutagenic purposes without modification of the reaction conditions or of the polymerase itself (Cadwell et al. (1992) "Randomization of genes by PCR mutagenesis" *Cold Spring Harbor Laboratory* 2: 28-33).

Consequently, despite the techniques developed, there remains, to date, a need for a random mutagenesis technique which is simple to implement, which does not involve the use of genotoxic chemical compounds or of complex steps, or the synthesis of numerous oligonucleotides, and which generates a sufficiently high frequency of random mutations to envisage the creation of a library of proteins.

DESCRIPTION OF THE INVENTION

After lengthy studies, the Applicant has demonstrated, surprisingly, that it is possible to use a mutase during the replication of a DNA, in order to obtain a sufficiently high frequency of random mutagenesis.

Document WO 98/23733 describes a method for identifying thermostable mutant polymerases having increased or decreased replication fidelity compared to a native polymerase. The possibility of using such mutant polymerases, the fidelity of which is decreased, in a method of random mutagenesis is very briefly mentioned, but no information is given, the document focusing on the identification of the mutants and on the use of the mutants having increased replication fidelity.

The invention thus relates to a method of random mutagenesis which comprises the replication of a DNA sequence in the presence of at least one mutase in effective amount. The DNA sequence may be a gene fragment or a complete gene, which can encode a protein, for example an enzyme.

Several mutases can be used, either simultaneously or successively. The mutase(s) used will preferably be thermostable. The mutases which can be used may be native polymerases, i.e. nonmutated polymerases, or optionally mutated mutases.

The term "mutase" is here intended to mean a DNA polymerase with a mutagenic level at least as high as that of DNA polymerase β (Pol β); in other words, a DNA polymerase at least as mutagenic as Pol β. Such a mutase will introduce unpaired nucleotides, a source of mutations during the replication of the DNA, in a random manner, into a gene or a gene fragment.

A suitable mutase can therefore be Pol β, or else Pol ι, Pol η or Pol κ.

DNA Pol β is a small polypeptide of 39 KD. It is an enzyme which is highly conserved in higher eukaryotes. Its primary function is thought to be the "at all costs" repair of damaged DNA, but it also has a role in the replication of native DNA. DNA Pol β is expressed at a constant level during the cell cycle, and exposure of the cells to xenobiotic agents, for example radiation, induces its expression.

To date, it has never been used in random mutagenesis. It differs from the DNA polymerases conventionally used in mutagenesis by virtue of its infidelity during DNA replication, this infidelity being thought to be related to the absence of associated corrective exonucleated activities (Kunkel T. A. (1985) "The mutational specificity of DNA polymerase-β during in vitro DNA synthesis" *J. Biol. Chem.* 260: 5787-5796; Kunkel, T. A. (1986) "Frameshift mutagenesis by eucaryotic DNA polymerases in vitro." *J. Biol Chem.* 261: 13581-13587). Unlike these other polymerases used, which exhibit insufficient infidelity to rapidly and easily generate random mutations which can result in the creation of mutated protein libraries, the degree of infidelity of Pol β is particularly high, and can reach $10^{-2}$.

Various sources of Pol β can be used: Hela cells (cell extracts), chicken, rat and human liver.

A native Pol β or a mutated Pol β can be used.

Whatever the mutase(s) used, the frequency of random mutagenesis is at least of the order of 1 mutation per 400 base pairs, preferably at least of the order of 1 mutation per 300 base pairs, more preferably at least of the order of 1 mutation per 200 base pairs, even more preferentially at least of the order of 1 mutation per 100 base pairs, or at least of the order of 1 per 50 base pairs.

The mutase(s) used will preferably be in the form of (a) cell extract(s).

The method according to the invention therefore comprises the replication of a DNA sequence in the presence of an effective amount of at least one mutase. Those skilled in the art will be able to define this effective amount. Due to the particular mutagenic properties of the mutase(s) used for the replication, copies of the starting DNA sequence are obtained which are not true copies, and which carry random mutations in sufficient number to generate a set of mutated polypeptides which can be used to create a polypeptide library and to select one or more polypeptides exhibiting one or more desired properties. The polypeptides can be proteins such as enzymes, of plant or animal, in particular human, origin. The desired property(properties) may, for example, be improved heat resistance, better effectiveness, a more rapid or more targeted action, binding or improved binding to a receptor, resistance or improved resistance for certain compounds, etc.

The replication step can be followed by a recombination step. This recombination can be a step of digestion of DNA followed by a PCR amplification step. In addition, during the PCR, the hybridization and polymerization steps can be combined in a single, very short step. The recombination can also be a step of digestion of DNA followed by a step of ligation of the digestion products.

The PCR, when it is used, therefore simply serves to amplify the material obtained at the end of the mutagenesis step. Preferably, use is then made of amplification primers the length of which is such that they require an amplification temperature of at least 70° C., which improves the specificity of the PCR.

The replication product, which carries (a) random mutation(s), and which is optionally recombined and amplified, can then be cloned into an expression vector in order to generate the mutated polypeptides, which are isolated. These mutated polypeptides will be grouped together in a polypeptide library, and may be selected as a function of the desired property or properties.

The mutagenic properties of the mutase(s) used may be further increased, in order to further increase the number of mutations generated. Several techniques are possible.

Thus, in one embodiment of the method according to the invention, magnesium is substituted with manganese or cobalt in the PCR reaction (Beckman et al. (1985) "On the fidelity of DNA replication: manganese mutagenesis in vitro." *Biochemistry* 24: 5810-5817).

Another embodiment of the method according to the invention comprises the use of a biased nucleotide pool, i.e. of a pool of nucleotides in which one or more nucleotides are favored relative to the others. By way of example, use may be made of a biased pool in which three of the natural nucleotides are favored relative to the fourth (Cadwell et al. (1992) "Randomization of genes by PCR mutagenesis." *Cold Spring Harbor Laboratory* 2: 28-33).

In another embodiment, one or more mutagenic nucleotide analogs are incorporated. Such an analog may be 8-oxoguanine (Zaccolo et al. (1996) "An approach to random mutagenesis of DNA using mixture of triphosphate derivatives of nucleoside analogues" *J. Mol. Biol.* 255: 589-603).

Use may also be made of another DNA polymerase in combination with the mutase(s), whether simultaneously or successively.

Finally, it is possible simply to modify one or more parameters of the reaction medium, such as the pH, the temperature or the salt concentration, in order to modify the action of the mutase(s). The present application is also directed toward any DNA and any polypeptide or protein obtained, or which can be obtained using a method according to the invention. It is in particular directed toward any library of DNA, of polypeptides or of proteins obtained, or which can be obtained by collection of DNA, polypeptides or proteins according to the invention. It is also directed toward any method for identifying a compound exhibiting an activity or property of interest, in particular in the medical, agrofoods or pharmaceutical field, characterized in that it comprises identifying, in a library according to the invention, a compound exhibiting said particular activity or property.

MORE DETAILED DESCRIPTION OF THE INVENTION

In the following examples, reference is made to the following figures:

FIG. 1 shows very schematically the steps of the method of producing random mutations, applied to an 85-mer polynucleotide, FIGS. 2A and 2B illustrate the results of migrations of the products thus obtained, FIG. 3 shows the spectrum of mutations thus engendered by polymerization of the 85-mer matrix, FIG. 4 shows schematically the production of random mutations in the lacZ gene carried by a plasmid vector, FIG. 5 shows very schematically the steps of a method of producing random mutations by replication of the lacZ gene encoding the α-peptide of β-galactosidase, carried by the plasmid pUC18, and FIG. 6 illustrates the distribution of the mutations thus engendered on the gene encoding the alpha-peptide of the lacZ gene, under standard conditions of replication with Pol β (all the dNTPs at 100 µm)

EXAMPLE 1

In vitro production of random mutations by replication of an 85-mer polynucleotide with DNA Pol β and use of a biased pool of deoxynucleotides.

FIG. 1 shows very schematically the various steps of the method, from the polynucleotide to the sequencing of the recombinant clones:

Material:

```
3' primer:
5' GATTGAATTCCTCATTATGG 3'           (SEQ ID NO: 1)

5' primer:
5' TGAATACTGTATGATAATCG 3'           (SEQ ID NO: 2)

85-mer matrix:
5' TGAATACTGTATGATAATCGTGAGGATCCCGCA (SEQ ID NO: 3)

TATAAGCTTTTCGATCGCCTGCAGTAACTCCACCAT

AATGAGGAATTCAATC 3'
```

Culture Media

Complete LB medium: 1% tryptone, 0.5% yeast extract, 1% Nacl, $H_2O$ qs 1 l. 15 g of agar are added to 1 liter of LB to prepare the LB/agar medium.

SOC medium: 2% tryptone, 0.5% yeast extract, 10 mM NaCl, 2.5 mM KCl, 10 mM $MgCl_2$, 10 mM $MgSO_4$, 20 mM glucose.

Bacterial Strain and Vectors

TABLE 4

| Strains | Genotypes | Sources |
|---|---|---|
| TOP 10 | F⁻ mcrA Δ(mrr-hsdRMS-mcrBc) Φ80lacZΔM15 ΔlacX74 recA1 deoR araD139 Δ (ara-leu) 7697 galU galK rpsL (Str$^R$) endA1 nupG | Invitrogen |
| BL21 | F⁻ ompT gal (dcm) (lon) hsdS$_B$ ($r_B^-$ $m_B^-$) with DE3, has λ prophage carrying the T7 RNA polymerase gene | BioLabs |

In Vitro Replication of the Matrix with DNA Pol β

Preparation and Purification of DNA Pol β

An overnight culture of the BL21 strain transformed with a plasmid expressing a Pol β: (His)$_6$ fusion protein under the control of a T7 promoter is diluted to 1/50 in LB medium+50 µg/ml Kanamycin, and incubated at 37° C. with shaking. At OD 0.6-1, 1 mM IPTG is added and the incubation is continued for 4 hours. The cells are centifuged and then lysed with lysosyme at 100 µg/ml and 0.1% triton X100. The lysis is carried out at 30° C. for 30 min. Next, the cells are sonicated and then centrifuged. The Pol β: (His)$_6$ fusion is purified on a nickel column and eluted with imidazole using the resin and the buffers of the Novagen purification kit.

Labeling of the 20-mer primer:

60 ng of the 5' primer are labeled with 10 units of $T_4$ polynucleotide kinase (New England BioLabs) for one hour at 37° C. in a buffer containing 70 mM Tris-HCl (pH 7.6), 10 mM $MgCl_2$, 5 mM dithiotreitol and 20 µCi $^{32}$P-γ-ATP. The enzyme is then inactivated by incubating the reaction mixture at 70° C. for 10 minutes.

Hybridization of the labeled primer to the matrix 60 ng of the 5' primer labeled with $^{32}$P-γ-ATP are added to 300 ng of the matrix in a hybridization buffer (100 mM Tris-HCl, 50 mM NaCl, 10 mM $MgCl_2$). The mixture is first denatured at 70° C. for 10 minutes. Hybridization of the two oligonucleotides is then obtained by continuing the incubation until the temperature of the bath has reached ambient temperature.

Replication of the Matrix

One unit of DNA Pol β is added to 5 ng of the 85-mer matrix hybridized to 20 ng of 20-mer oligonucleotide labeled with $^{32}$P-γ-ATP, in a reaction mixture containing 25 mM HEPES (pH 8.5), 125 mM NaCl, 5 mM $MgCl_2$, 200 µM dATP, 200 µM dGTP and 200 µM dTTP. These various mixtures are distributed into five tubes to which various concentrations of dCTP (0 dCTP, 0.2 µM dCTP, 2 µM dCTP, 20 µM dCTP, 200 µM dCTP) are added. After incubation for one hour at 37° C., part of the mixture is loaded onto an acrylamide gel (15% acrylamide, 7 M urea, 30% formamide) in order to control the reaction products. The other part is supplemented with dCTP at a final concentration of 200 µM and the reaction is continued for one hour. Finally, the reaction is stopped with the stop buffer (90% formamide/0.1% xylene cyanol/0.1% bromophenol blue/0.1 mM EDTA). The samples are then denatured for 10 minutes at 70° C. and loaded onto an acrylamide gel in order to visualize the replication products. These products are revealed by exposure on an autoradiographic film.

Polymerase Chain Reaction (PCR)

The PCR reaction was carried out by adding 1 µl of the replication product obtained by the action of Pol β to a mixture containing the polymerization buffer (20 mM Tris HCl (pH 8.8), 10 mM KCl, 10 mM $(NH_4)_2SO_4$, 0.1% Triton) (New England Biolabs), 1.5 mM $MgSO_4$, 200 mM dNTP, 20 pmol of each 5' and 3' oligonucleotide, and 5 u of high fidelity Vent polymerase (New England Biolabs). These mixtures were incubated in a BioRad thermocycler according to the following program: (95° C, 5 min)-(95° C. 30 sec.-50° C. 30 sec.-72° C. 30 sec.)×30 cycles-(72° C.-5 min.). The PCR products are then loaded onto a 1% TAE agarose gel. After migration and staining of the gel with ethidium bromide, the 85-mer band corresponding to the product of amplification of the matrix is visualized by trans-illumination with ultraviolet light.

Cloning

The cloning of the amplification products was carried out using the Zero Blunt TOPO PCR Cloning Kit from Invitrogen. 1 µl of amplification product obtained by PCR is added to 10 ng of the cloning vector pCR-Blunt II-TOPO (Invitrogen) contained in the following buffer: 50% glycerol, 50 mM Tris-HCl, 1 mM EDTA, 2 mM DTT, 0.1% Triton X-100, 100 µg/ml BSA. The mixture is maintained at ambient temperature for five minutes and then incubated at 4° C. 2 µl of the cloning reaction are then added to Top 10 competent cells (Invitrogen), and incubated for 30 minutes at 4° C. A heat shock is carried out at 42° C. for 30 seconds. The cells are then again placed on ice before being incubated at 37° C. for one hour in 250 µl of SOC medium. Finally, the transformants are selected on LB/agar medium containing 50 µg/ml of kanamycin.

Extraction of the Plasmidic DNA

The recombinant plasmids are extracted and purified with the Quia Prep Spin system from Quiagen. The plasmids are eluted in 50 µl of sterile water and controlled on a gel of 1% agarose in 1×TAE, after staining with ethidium bromide and illumination by ultraviolet radiation.

Sequencing

The sequencing reaction is carried out with the SequiTherm EXCEL II DNA sequencing Kits-LC system from Epicentre Technologies. 1 pmol of M13 primer labeled with IRD700 (MWG Biotech) and 300 ng of recombinant plasmids are incubated with 1U of Sequitherm EXCEL II DNA polymerase in the Sequitherm EXCEL II sequencing buffer (Epicentre Technologies). This mixture was incubated in a PTC-100 thermocycler (MJ Research, Inc.) according to the following program: (95° C. 5 min.)-(95° C. 30 sec.-57° C. 15 sec.-70° C. 1 min.)×30 cycles-(70° C.-10 min.). The reaction products are then loaded onto a sequencing gel and analyzed using a LONG READIR 4200 sequencer (Li-COR).

FIG. 2 shows the result of the migration of the products of replication with Pol β. Part A represents the results after replication for one hour with the various concentrations of dCTP (1=0 µM, 2=0.2 µM, 3=2 µM, 4=20 µM, 5=200 µM) and 200 µM of each of the other dNTPs (dATP, dGTP, dTTP). In part B, lanes 6, 7, 8 and 9 represent the products of replication 1, 2, 3 and 4, respectively, after complementation of dCTP at a concentration of 200 µM and continuation of the reaction for one hour.

Table 1 below gives a summary of the production of random mutations by DNA Pol β on an oligonucleotide. It comprises the frequencies of the mutations generated by replication with DNA Pol β under standardized conditions and using a biased pool of deoxyribonucleotides.

TABLE 1

| dCTP | dATP | dGTP | dTTP | Sequenced clones | Mutation frequencies |
|---|---|---|---|---|---|
| 200 µM | 200 µM | 200 µM | 200 µM | 26 | $0.9 \times 10^{-2}$ |
| 20 µM | 200 µM | 200 µM | 200 µM | 26 | $1.2 \times 10^{-2}$ |
| 2 µM | 200 µM | 200 µM | 200 µM | 27 | $1.36 \times 10^{-2}$ |
| 0.2 µM | 200 µM | 200 µM | 200 µM | 20 | $1.7 \times 10^{-2}$ |
| 0 µM | 200 µM | 200 µM | 200 µM | 18 | $1.8 \times 10^{-2}$ |

The experiment under standardized conditions of polymerization with Pol β (the 4 dNTPs are present at a concentration of 200 µM) shows a high mutation frequency, approximately one mutation every 100 nucleotides replicated, thus confirming the mutagenic capacity of this polymerase lacking fidelity.

Pol β is capable of completely replicating the 85-mer matrix, even in the absence of one type of nucleotide out of four. These replication reactions result in an increase in the rate of mutations which is inversely proportional to the concentration of the fourth nucleotide dCTP (table 1). This confirms the potentialization of the mutagenic capacity of Pol β by the combination of a nucleotide bias in the reaction medium.

Even in the absence of a biased pool of nucleotides, the frequency of the mutations observed is $0.9 \times 10^{-2}$, that is to say close to 1 per 100 base pairs.

In addition, these mutations are distributed throughout the length of the matrix, and in a random manner. The mutagenesis is not therefore confined to specific sites.

FIG. 3 represents the spectrum of mutations engendered by the polymerization of the 85-mer matrix with Pol β under the following conditions: 200 µM of dATP, dGTP and dTTP, and 0 µM of dCTP.

EXAMPLE 2

In vitro production of random mutations in the lacZ gene carried by a plasmid vector.

The aim of this experiment is to perform SV40 replication of a pBK-CMV matrix (containing the SV40 origin, the Neo$^r$-Kan$^r$ double resistance gene and the sequence encoding the α-peptide of β-galactosidase allowing α-complementation in Δα-lacZ strains) with Hela extracts and the T antigen, and to add purified rat DNA Pol β during the experiments. The difference in frequency of mutagenesis induced by the excess of Pol β is measured using the mutagenesis test described below (white/blue screen).

Bacterial Strains, Plasmids, Restriction Enzymes

The plasmid pBK-CMV (Strategene) was amplified in a dam$^+$ bacterium (DH5α) and purified using the Wizard Plus DNA Purification System (Promega). The DpnI enzyme comes from BioLabs.

TABLE 5

| Strains | Genotypes | Sources |
|---|---|---|
| MC1061Mut S | F$^-$ araD139 Δ(araleu)7696 galE15 galk16 ΔlacX74 rpsL (Str$^R$) hsdR2($r_K^-$ $m_K^+$) mcrA mcrB1 [mutS : :Tn10] | T. Kunkel, USA |
| JM109 | F' traD36 lacI$^q$ Δ(lacZ)M15 proA + B + /e14$^-$ (McrA$^-$) Δ(lac-proAB) thi gyrA96 (Nal$^r$) endA1 hsdR17 ($r_K^- m_K^+$) relA1 supe44 | T. Kunkel, USA |
| DH5α | EndA1 hsdR17 ($r_K^- m_K^+$) supE44 thi-1 recA1 gyrA (Nal$^r$) relA1 Δ(lacIZYA-argF)U169 deoR (φ80dlacΔ(lacZ)M15) | BioLabs |

Preparation of the Replicative Cell Extracts Derived from Hela Cells

The cell extracts were prepared according to the procedure developed by Robert et al. (Robert et al. (1993) "Chromosome and gene analysis" *Methods in Molecular Genetics*. Adolph, K. W. Ed. 2: 295-313). Hela cells in suspension are cultivated in 4 liters of RPMI1640 supplemented with 9% serum and Pen/Strep5500, harvested in the exponential phase, and centrifuged at 1 500 rpm for 5 min. at ambient temperature. They are washed in 200 ml of 1×PBS at 4° C. and centrifuged at 1 500 rpm for 5 min. at 4° C. The cells are washed in 25 ml of an isotonic medium at 4° C. (20 mM Hepes-KOH, pH 7.5, 5 mM KCl, 1.5 mM MgCl$_2$, 0.5 mM DTT, 250 mM sucrose) and centrifuged at 4 000 rpm for 10 min. at 4° C. They are taken up in hypotonic medium at 4° C. without sucrose (20 mM Hepes-KOH, pH 7.5, 5 mM KCl, 1.5 mM MgCl$_2$, 0.5 mM DTT) and then centrifuged. They are then lysed in a potter homogenizer after adding 50 µl of aprotinin at 1.5 mg/ml, and then centrifuged at 10 000 rpm for 20 min at 4° C. The supernatant is then centrifuged at 50 000 rpm for 60 min at 4° C., and then aliquoted and frozen in liquid nitrogen. The amount of proteins present is assessed according to the Bradford method, using BSA to establish the standard calibration range.

SV40 Replication

This replication step was carried out using the assay developed by Robert et al. The SV40 replication reaction is carried out at 37° C. for 6 h in a final reaction volume of 25 µl containing 30 mM HEPES-KOH, pH 7.8/7 mM MgCl$_2$/0.5 mM DDT/200 µM CTP, GTP, UTP/4 mM ATP/100 µM dCTP, dGTP, dTTP/40 mM creatine phosphate/100 µg/ml creatine phosphokinase/100 ng pBK-CMV/400 µg of Hela replicative extracts/0.5 µg Large T Antigen to which are added +/–5 µg (i.e. 1.2 U) of Pol β. The replication reaction is stopped by adding 25 µl of a buffer containing 2 mg/ml PK, 50 mM EDTA and 2% SDS, and incubating at 55° C. for 60 min. The DNA is purified by extraction with phenol, phenol/chloroform/isoamile alcohol, and ether, and then precipitated with 2.5 V 100% ethanol, 0.1 V sodium acetate and 1 µg of glycogene, and centrifuged at 13 000 rpm for 30 min. at 4° C. The DNA is then washed with 70% ethanol, centrifuged (13 000 rpm, 15 min., 4° C.) and digested with 10 U of DpnI for 2 h in order to remove any pBK-CMV matrix which has not been replicated at least once by the Hela extracts. It is finally reprecipitated and taken up in 10 µl of H$_2$O.

Analysis of the Mutagenesis

2 µl of replicated plasmid are electroporated into the strain MC1061MutS, which is deficient for the mismatch repair system, in order to fix the mutations, and then the plasmid is amplified by selecting the electroporated population with Kanamycin (50 µg/ml) on a total volume of 20 ml of LB. The plasmid is extracted using the Wizard Plus DNA Purification System (Promega) and then 100 ng is electroporated into the strain JM109 allowing α-complementation. A suitable volume of the bacterial population (containing approximately 2 000 to 3 000 clones) is then inoculated into 7 ml of soft LB containing 1.6 mg of X-Gal, 1.6 mg of IPTG and 350 µg of Kanamycin, and then plated out onto dishes 14 in diameter containing 40 ml of LB/agar with 50 µg/ml of Kanamycin. The frequency of mutagenesis present on the replicated plasmid is deduced from the number of white colonies compared to the number of total colonies present on the dish.

FIG. 4 shows the summary of this production of random mutations.

Table 2 below shows the results of the production of random mutations.

TABLE 2

| DNA substrate | Colonies examined | | Mutations × 10$^{-3}$ |
| --- | --- | --- | --- |
|  | Total | Mutants |  |
| Nonreplicated DNA (no (AgT) | 28 640 | 184 | 6.4 |
| DNA replicated by cell extracts without Pol β | 141 390 | 918 | 6.5 |
| DNA replicated by cell extracts with Pol β | 209 762 | 2 953 | 14 |

It shows that, under physiological conditions, i.e. in the presence of cell extracts, Pol β is capable of inducing random mutations on a mutagenesis target carried by a plasmid replication substrate. Once again, it is immediately noted that the frequency of the mutations induced is high, in this case 1.4 10$^{-2}$, i.e. more than 1 per 100 base pairs.

EXAMPLE 3

Replication of the lacZ Gene by Pol β and Comparison with the Results Obtained by PCR with a taq Polymerase This example shows that Pol β introduces a frequency of mutagenesis 50 times higher than that obtained with taq polymerase by PCR.

Random mutations were produced in vitro by replication of the lacZ gene encoding the α-peptide of β-galactosidase, carried by the plasmid pUC18 (invitrogen), with DNA polymerase β, and use of a biased pool of deoxynucleotides. FIG. 5 shows very schematically the various steps of the method followed, from the replication of the lacZ gene with the polymerase β to the sequencing of the mutant clones.

Material:

```
                                              (SEQ ID NO: 4)
5' primer:
5' CGCGACTCATGCGACGCATTACGAATTCGAGCTCGGTAC 3'

(SEQ ID NO: 5)
3' primer
5' CACTCGACGCTGATGCAGTGCACCATATGCGGTGTG 3'
```

The parts underlined are the sequences complementary to the sequences in the 5' and 3' positions flanking the lacZ gene carried by the plasmid pUC18.

Culture Media

The composition of the Medium is Detailed in Example 1.

Bacterial Strain

The genotype and the origin of the strain Top 10 are described in example 1.

In Vitro Replication of the lacZ Gene with DNA Polymerase β

1 µg of plasmid pUC18 is added to 10 pmol of the 5' and 3' primers in 15 µl of replication buffer (50 mM Tris-HC1, pH 8.8, 10 mM MgCl$_2$, 100 mM KCl, 0.4 mg/ml BSA, 1 mM DTT, 10% glycerol, Trevigen). The mixture is denatured for 5 min. at 90° C. and then hybridized for 2 min. at 55° C., before being conserved at 4° C. A solution of 15 µl of the same buffer containing 4 units of polymerase β (Trevigen), 0.5 mM Mn2+ and 100 µM of each of the 4 natural deoxynucleotides is then added to the 15 µl of hybridization mixture. The reaction of replication by polymerase β is then carried out at 37° C. for one hour. In other polymerization reactions, the pool of the 4 deoxynucleotides is biased by a lower concentration of one of the 4 deoxynucleotides compared to the three others. The replication products are then extracted with phenol-chloroform.

Selective PCR

The selective PCR reaction is carried out by adding 1 µl of the replication product (diluted to 1/10), obtained by the action of the polymerase β, to a mixture containing the PCR buffer (20 mM Tris HCl pH 8.4, 50 mM KCl) (Life Technologies), 1.5 mM MgCl$_2$, 10 pmol of the 5' and 3' primers, 200 µM of the 4 dNTPs and 1.25 U PLATINUM Taq DNA polymerase (Life Technologies). This mixture is incubated in a thermocycler (Eppendorf) according to the following program: (95° C., 5 min.)-(94° C., 15 sec.-55° C., 30 sec.-72° C., 30 sec.)-(94° C., 15 sec.-72° C., 30 sec.)+30 cycles-(72° C., 10 min.). This program makes it possible to specifically amplify the DNA fragments synthesized by the polymerase β.

The PCR products are then extracted with phenol-chloroform, precipitated with ethanol, and recovered in TE (10 mM Tris HCl pH 8, 1 mM EDTA).

Cloning of the PCR Products

Before being cloned into pUC18, the PCR products are digested with 20 U of NdeI (BioLabs) and 10 U BamH1 (Q-BIOgene) in a digestion buffer containing (50 mM NaCl, 10 mM Tris-HCl, 10 mM MgCl$_2$, 1 mM DTT and 100 µg/ml BSA) for one hour at 37° C. The digestion product is then purified with the GenClean2 kit (BIO 101) after migration on agarose gel and excision of the band containing the PCR product. The PCR product is then cloned into pUC18 (predigested with NdeI and BamH1) subsequent to a ligation (16° C. overnight) with 40 U of T4 DNA ligase (BioLabs) in a buffer containing (50 mM Tris HCl pH 7.5, 10 MM MgCl$_2$, 10 mM DTT, 1 mM ATP and 25 µg/ml BSA). The ligation product is then precipitated with ethanol and taken up in 5 µl of TE (10 mM Tris HC1 pH 8, 1 mM EDTA). 2 µl of the ligation reaction are then added to the Top 10 competent cells (Invitogen) and incubated for 30 minutes at 4° C. A heat shock is carried out at 42° C. for 30 seconds. The cells are then again placed in ice before being incubated at 37° C. for one hour in 250 µl of SOC medium. Finally, the transformants are selected on LB/agar medium containing 100 µg/ml of ampicillin and 60 µg/ml of X-Gal (5-bromo-4-chloro-3-indoxyl-beta-D-galactopyranoside, Euromedex). The frequency of mutants is deduced from the number of white colonies compared to the number of total colonies present on the dish.

Figure 1:
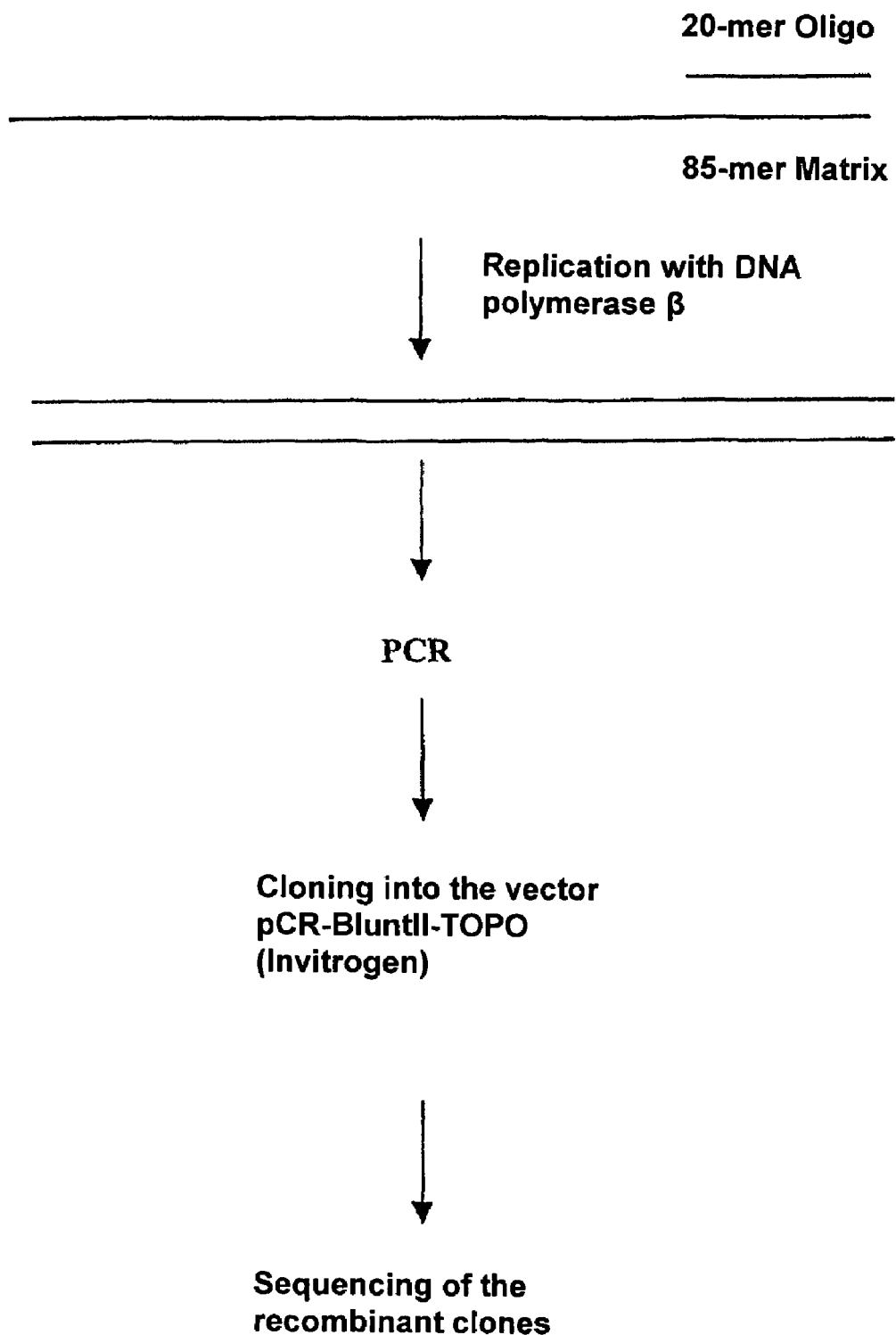
Figure 2:
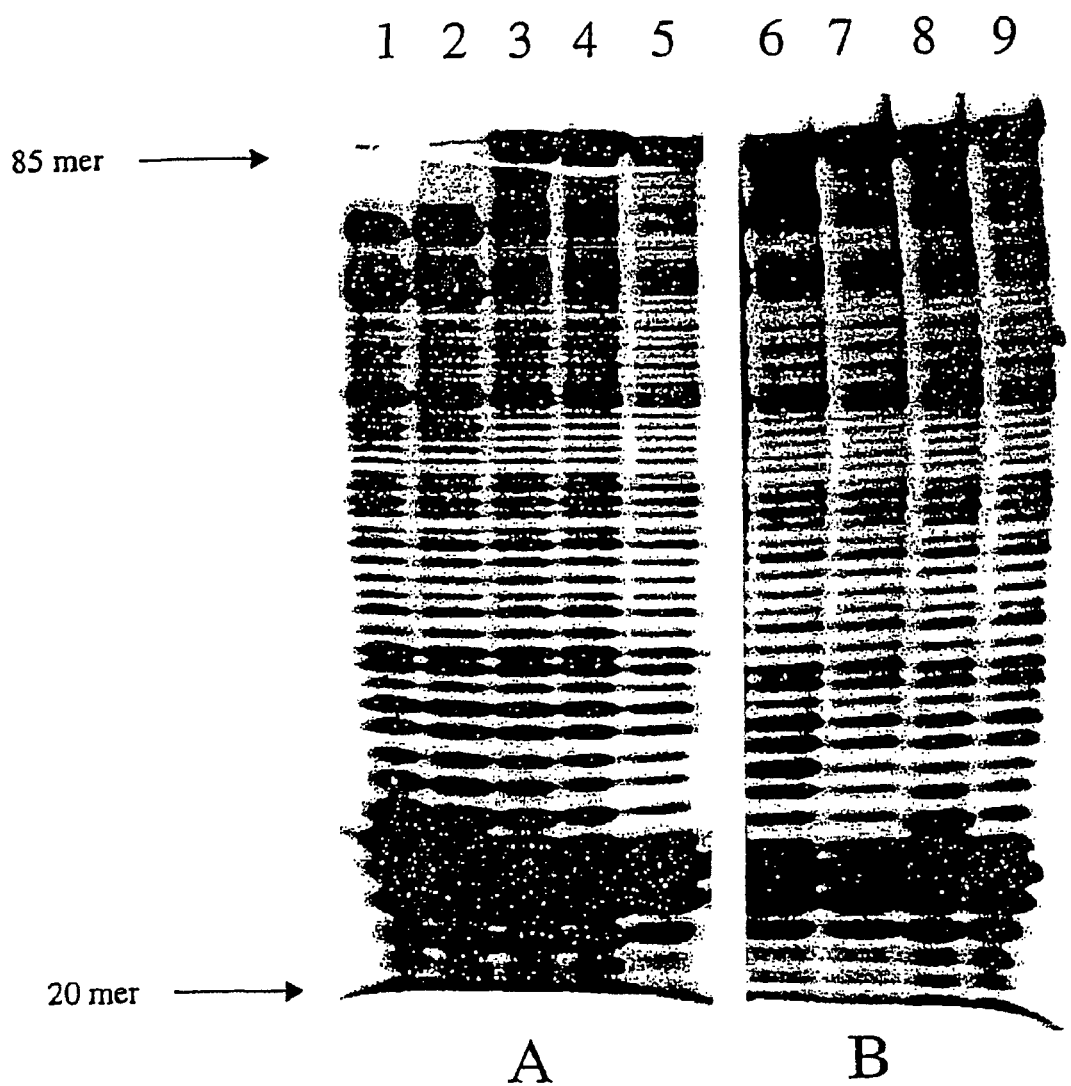
Figure 4:
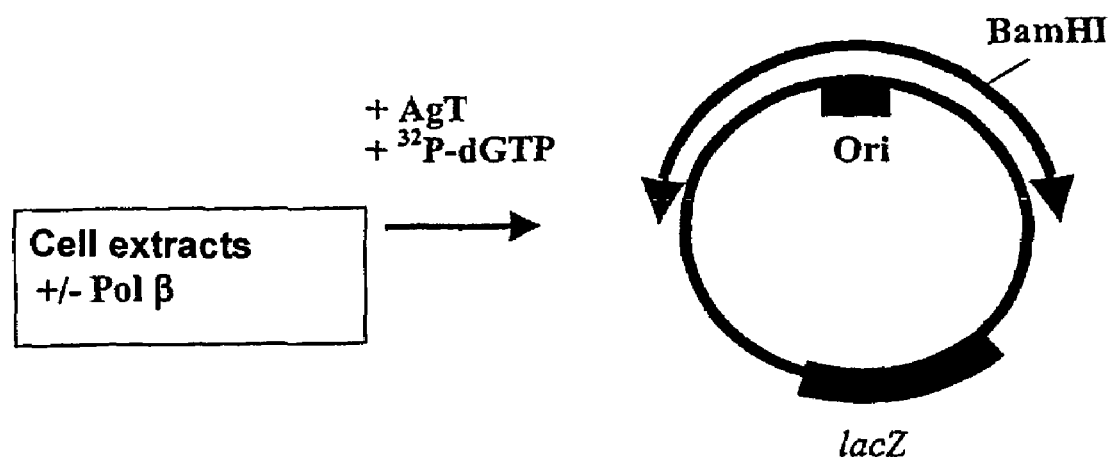
Figure 5:
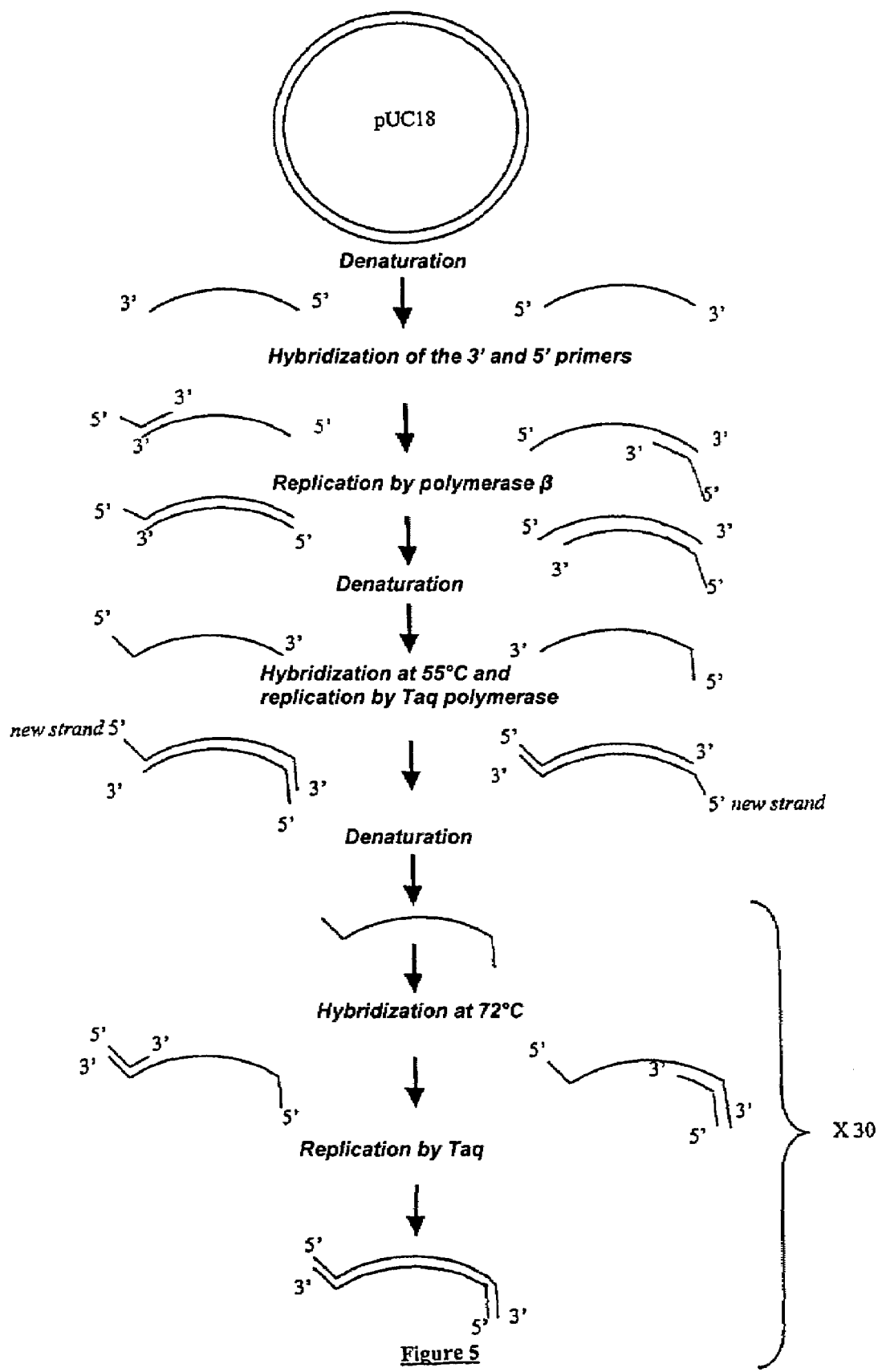
FIG. 5 shows the summary of this production of random mutations.
Figure 6:
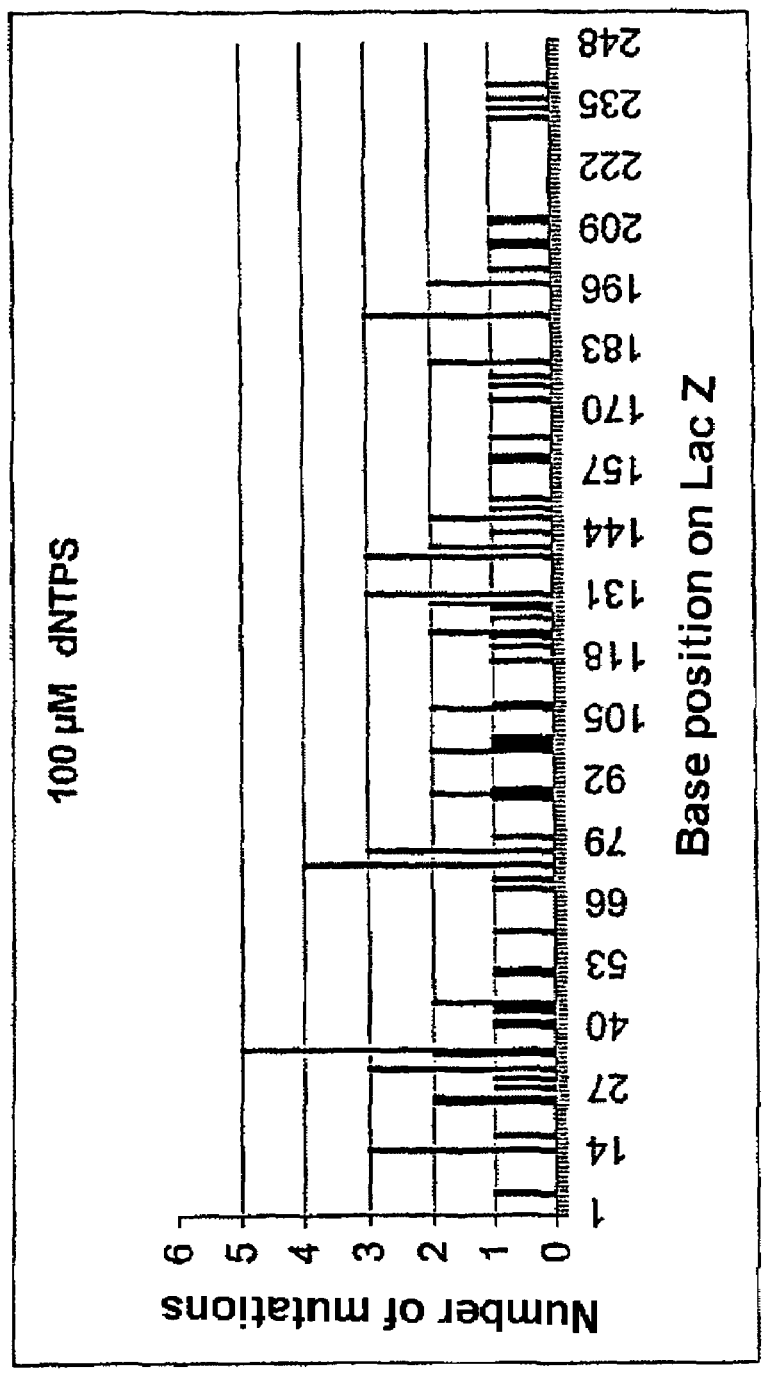
FIG. 6 illustrates the distribution of the mutations thus engendered on the gene encoding the alpha-peptide of the lacZ gene, under the standard conditions for replication with Pol β (all the dNTP at 100 µM).

Table 3 below shows a summary of production of random mutations.

TABLE 3

|  | Clones screened | Mutants | Mutation frequency (%) | Mutations/kb |
|---|---|---|---|---|
| Replication by Taq (100 µM dNTPS) | 2 908 | 14 | 0.48 | ND |
| Replication by Pol β (100 µM dNTPs) | 764 | 187 | 24.48 | 17.09 |
| Replication by Pol β (100 µM dATP, 100 µM dGTP, 100 µM dCTP, 20 µM dTTP) | 1 749 | 730 | 41.74 | 18.47 |
| Replication by Pol β (100 µM dGTP, 100 µM dCTP, 100 µM dTTP, 20 µM dATP) | 1 734 | 1 078 | 62.17 | 23.6 |

This summary shows that, under normal conditions, i.e. when the replication with polymerase β is carried out with 100 µM of each of the four dNTPs, the polymerase β is capable of producing random mutations on the gene encoding β-galactosidase. This rate of mutation (24.48%), compared to that produced by PCR amplification using the taq polymerase (Life Technologies) (0.48%), is 50 times higher. This very high rate of mutation produced by polymerase β makes it possible to screen a smaller number of mutants with the aim of isolating a mutant of a protein whose activity is enhanced or weakened. This frequency of mutants is even higher when the concentration of one of the four dNTPS is modified. For example, when the dTTP or the dATP is used separately in two independent reactions at a concentration of 20 µM, the frequency of mutants obtained is 41.7% and 62.17% respectively. This increase in frequency of mutants makes it possible to reduce even further the number of mutants to be screened.

The results of these various experiments demonstrate the relevance of using this enzyme, which is in particular native, for the purpose of creating random mutants, and make it possible to envision designing a tool based on the use of Pol β or of cell extracts/Pol β for the purpose of modifying any sequence carried by a plasmid vector.

The invention claimed is:

1. A method of random mutagenesis comprising steps of:
   (i) replicating a DNA sequence with an effective amount of at least one mutase in order to generate random mutations within the replicated DNA sequence, wherein the at least one mutase is selected from the group consisting of DNA polymerases beta, iota, eta and kappa;
   (ii) amplifying by PCR the replicated DNA using a DNA polymerase other than those recited in step (i);
   (iii) cloning the amplified DNA sequence into an expression vector; and
   (iv) generating a library of mutated polypeptides.

2. The method of claim 1, wherein the at least one mutase is DNA polymerase beta.

3. The method of claim 1, wherein the at least one mutase is used in the form of a cell extract.

4. The method of claim 1, wherein several mutases selected from the group consisting of DNA polymerases beta, iota, eta and kappa are used simultaneously in the DNA replication in step (i).

5. The method of claim 1, wherein several mutases selected from the group consisting of DNA polymerases beta, iota, eta and kappa are used successively in the DNA replication in step (i).

6. The method of claim 1, wherein random mutations within the replicated DNA sequence are generated with a frequency at least of the order of 1 mutation per 400 base pairs.

7. The method of claim 6, wherein the frequency is at least of the order of 1 mutation per 300 base pairs.

8. The method of claim 7, wherein the frequency is at least of the order of 1 mutation per 200 base pairs.

9. The method of claim 8, wherein the frequency is at least of the order of 1 mutation per 100 base pairs.

10. The method of claim 9, wherein the frequency is at least of the order of 1 mutation per 50 base pairs.

11. The method of claim 9, wherein the DNA replication in step (i) is followed by a recombination step.

12. The method of claim 1, wherein nucleotides selected from the group consisting of a biased nucleotide pool, one mutagenic nucleotide analog, several mutagenic nucleotide analogs and/or any combination thereof are used in the DNA replication in step (i).

13. The method of claim 1, wherein an element selected from the group consisting of manganese and cobalt is used during the PCR amplification of step (ii).

14. The method of claim 1, wherein cloning the amplified DNA sequence into an expression vector comprises steps of:
    synthesizing the mutated polypeptides; and
    isolating the mutated polypeptides synthesized.

15. The method of claim 14, wherein the amplified DNA sequence is recombined before being cloned.

16. The method of claim 14, wherein mutated polypeptides exhibiting a desired property or desired properties are selected.

17. The method of claim 1, wherein the DNA replication in step (i) involves replicating a DNA sequence carried by a plasmid.

18. The method of claim 1, wherein the DNA replication in step (i) is stopped with a stop buffer prior to commencement of the PCR amplification in step (ii).

19. The method of claim 1, wherein the DNA replication in step (i) is carried out a temperature less than 70°C., and the PCR amplification in step (ii) is carried out at a temperature greater than 70°C.

20. The method of claim 1, wherein the polymerase used for the DNA replication in step (i) is stable only at a temperature less than 70°C., and the polymerase used for the PCR amplification in step (ii) is stable at a temperature greater than 70°C.

21. A method of random mutagenesis comprising steps of:
    (i) replicating a DNA sequence with an effective amount of at least one mutase to generate random mutations within the replicated DNA sequence, wherein the at least one mutase is selected from the group consisting of DNA polymerases iota, eta and kappa;
    (ii) amplifying by PCR the replicated DNA using a DNA polymerase other than those recited in step (i)
    (iii) cloning the amplified DNA sequence into an expression vector; and
    (iv) generating a library of mutated polypeptides.

* * * * *